(12) United States Patent
Cheng et al.

(10) Patent No.: US 9,791,387 B2
(45) Date of Patent: Oct. 17, 2017

(54) INSPECTION SYSTEM AND METHOD FOR CONTROLLING THE SAME

(71) Applicant: Test Research, Inc., Taipei (TW)

(72) Inventors: Yu-Che Cheng, Taipei (TW); Chia-Ho Yen, Taoyuan County (TW); Shih-Liang Chen, Taipei (TW); Chih-Pin Chiu, New Taipei (TW)

(73) Assignee: Test Research, Inc., Taipei (TW)

( * ) Notice: Subject to any disclaimer, the term of this patent is extended or adjusted under 35 U.S.C. 154(b) by 69 days.

(21) Appl. No.: 14/497,337

(22) Filed: Sep. 26, 2014

(65) Prior Publication Data

US 2016/0091441 A1    Mar. 31, 2016

(51) Int. Cl.
*G01N 23/083* (2006.01)
*G01T 7/10* (2006.01)

(52) U.S. Cl.
CPC ............ *G01N 23/083* (2013.01); *G01T 7/10* (2013.01)

(58) Field of Classification Search
CPC .. G01V 5/0016; G01V 5/0066; G01V 5/0008; G01N 2223/639; G01N 2223/643
See application file for complete search history.

(56) References Cited

U.S. PATENT DOCUMENTS

| | | | | |
|---|---|---|---|---|
| 6,324,249 | B1* | 11/2001 | Fazzio | G01N 23/04 378/22 |
| 7,099,432 | B2 | 8/2006 | Ichihara et al. | |
| 7,430,271 | B2* | 9/2008 | Griffith | A61B 6/032 378/21 |
| 7,529,336 | B2 | 5/2009 | Wen et al. | |
| 8,254,519 | B2 | 8/2012 | Sugita et al. | |
| 2003/0058993 | A1* | 3/2003 | Bohn | G01N 23/04 378/68 |
| 2004/0109532 | A1* | 6/2004 | Ford | G01N 23/046 378/57 |
| 2005/0074088 | A1* | 4/2005 | Ichihara | G01N 23/046 378/58 |
| 2011/0255660 | A1 | 10/2011 | Masuda et al. | |
| 2012/0119109 | A1 | 5/2012 | Kim et al. | |

FOREIGN PATENT DOCUMENTS

| | | |
|---|---|---|
| CN | 101839871 A | 9/2010 |
| DE | 102010010723 A1 | 9/2011 |
| JP | 05-172763 A | 7/1993 |

(Continued)

OTHER PUBLICATIONS

Levakhina, Y. M. et al., "A dual-axis tilt acquisition geometry for digital musculoskeletal tomosynthesis" In: Physics in Medicine and Biology 58 (2013), 4827-4848.

*Primary Examiner* — Hoon Song
(74) *Attorney, Agent, or Firm* — CKC & Partners Co., Ltd.

(57) ABSTRACT

An inspection system includes an irradiation source, an image detector, and a placement device. The placement device comprises a carrier and a rotation mechanism. With respect to connections, the placement device is configured to be disposed between the irradiation source and the image detector, and the rotation mechanism is configured to be connected to the carrier. With respect to operations, the irradiation source and the image detector are driven to be moved along a predetermined path, the carrier is configured to carry at least one object, and the rotation mechanism is configured to rotate the carrier.

18 Claims, 9 Drawing Sheets

(56) References Cited

FOREIGN PATENT DOCUMENTS

| | | |
|---|---|---|
| JP | 2001-324456 A | 11/2001 |
| JP | 2003-329616 A | 11/2003 |
| JP | 2004-132931 A | 4/2004 |
| JP | 2005-331428 A | 12/2005 |
| JP | 2009-063387 A | 3/2009 |
| JP | 2010-156607 A | 7/2010 |
| TW | M479727 U | 6/2014 |

* cited by examiner

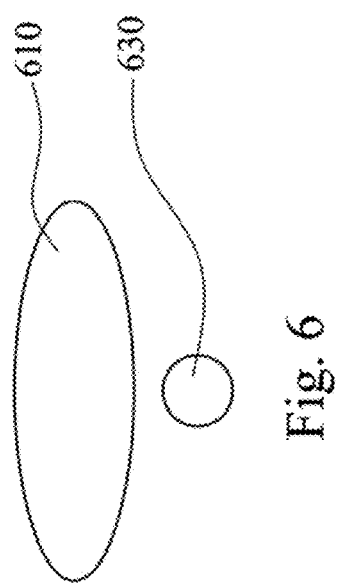

INSPECTION SYSTEM AND METHOD FOR CONTROLLING THE SAME

BACKGROUND

Field of Invention

The present invention relates to a detection system and a method for controlling the detection system. More particularly, the present invention relates to an inspection system and a method for controlling the inspection system.

Description of Related Art

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure.

Among the NDI technology, X-ray laminography is an imaging technique that generates cross-sectional images of selected planes within a test object for inspection. Conventionally, the X-ray laminography system includes an X-ray source, X-ray detectors defining an image plane, and a fixture base for placement of the test object to be scanned between the X-ray source and the detectors.

However, the image obtained by the X-ray laminography system is limited by the mechanism of the X-ray laminography system itself. For example, the test object is placed on the fixture base, and the X-ray source is disposed on the top of the test object to irradiate the X-ray through the test object. If another object is placed under the test object, said another object will be blocked by the test object. Furthermore, if another object induced a detected defect of the test object, the defect of the test object will be ignored by the X-ray laminography system due to the defect being blocked by the test object.

In view of the foregoing, there exist problems and disadvantages in the existing products that await further improvement. However, those skilled in the art sought vainly for a solution.

SUMMARY

The following summary presents a simplified summary of the disclosure in order to provide a basic understanding to the reader. This summary is not an extensive overview of the disclosure and it does not identify key/critical elements of the present invention or delineate the scope of the present invention.

One aspect of the present disclosure is directed to an inspection system. The inspection system includes an irradiation source, an image detector, and a placement device. The placement device includes a carrier and a rotation mechanism. With respect to connections, the placement device is configured to be disposed between the irradiation source and the image detector, and the rotation mechanism is configured to be connected to the carrier. With respect to operations, the irradiation source and the image detector are driven to be moved along a predetermined path, the carrier is configured to carry at least one object, and the rotation mechanism is configured to rotate the carrier.

Another aspect of the present disclosure is directed to a method for controlling an inspection system. The inspection system includes an irradiation source, an image detector, and a placement device configured to be disposed between the irradiation source and the image detector, and the placement device includes a carrier and a rotation mechanism. The method includes:

driving the irradiation source and the image detector to move along a predetermined path;

carrying an object by the carrier; and rotating the carrier by the rotation mechanism.

In view of the foregoing, embodiments of the present disclosure provide an inspection system and a method for controlling the same to improve the problem that if one object is blocked by another from X-ray beam, said object cannot be detected by the X-ray laminography system.

These and other features, aspects, and advantages of the present invention, as well as the technical means and embodiments employed by the present invention, will become better understood with reference to the following description in connection with the accompanying drawings and appended claims.

BRIEF DESCRIPTION OF THE DRAWINGS

The invention can be more fully understood by reading the following detailed description of the embodiment, with reference made to the accompanying drawings as follows:

FIG. 6 is an inspection result diagram of an inspection system according to embodiments of the present invention;

Figure 1:
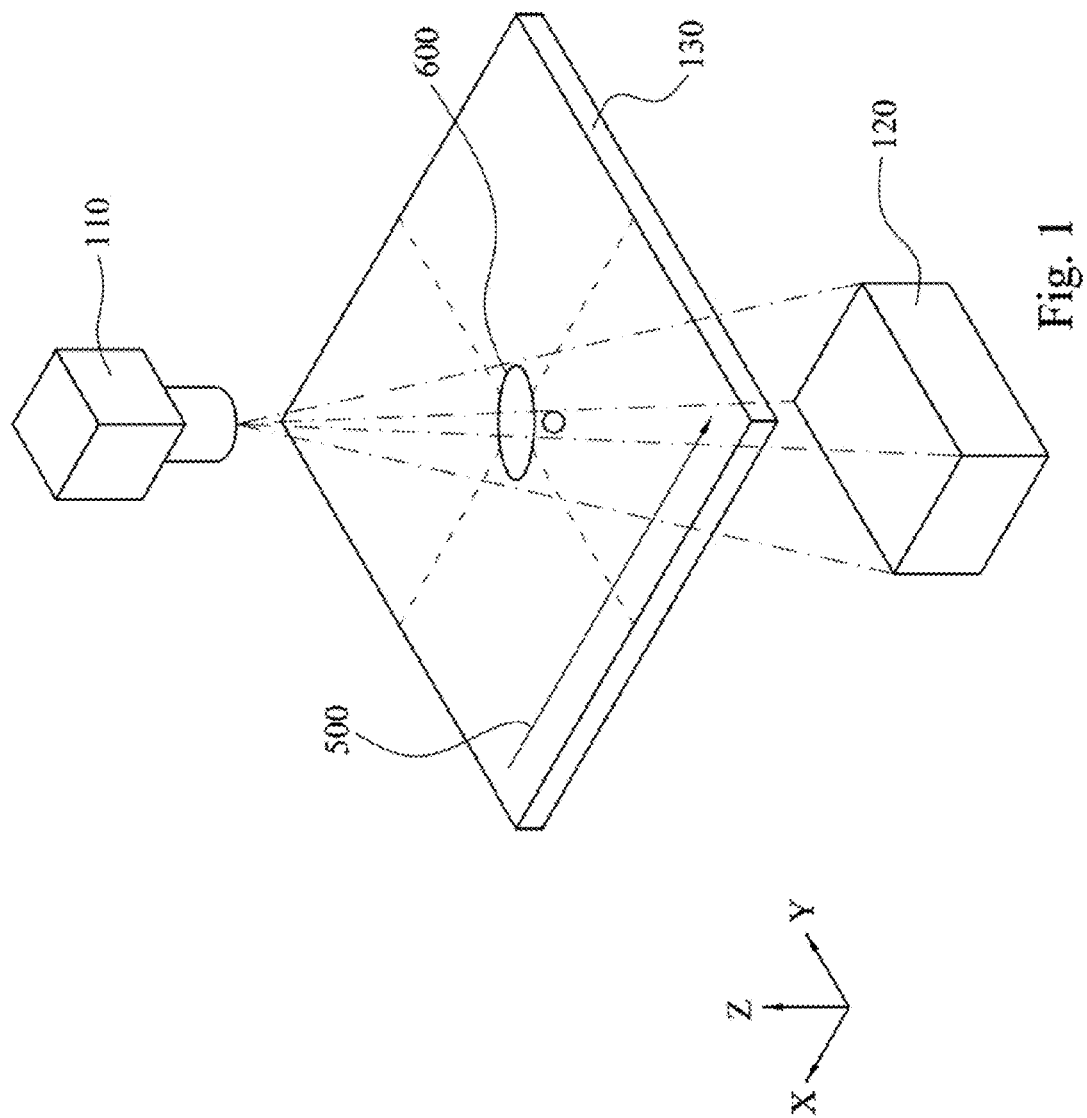
FIG. 1 is a schematic diagram of an inspection system according to embodiments of the present invention.

In accordance with common practice, the various described features/elements are not drawn to scale but instead are drawn to best illustrate specific features/elements relevant to the present invention. Also, wherever possible, like or the same reference numerals are used in the drawings and the description to refer to the same or like parts.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular.

FIG. 1 is a schematic diagram of an inspection system according to embodiments of the present invention. As shown in FIG. 1, the inspection system includes an irradiation source 110, an image detector 120 which can be but not limited to a plurality linear detectors or an area detector, and a placement device 130. With respect to connections, the placement device 130 is configured to be disposed between the irradiation source 110 and the image detector 120.

With respect to operations, the placement device 130 is configured to carry an object 600 for inspection. The irradiation source 110 is configured for irradiating radiation, for example, X-ray beam, to pass through the object 600. The image detector 120 is configured to capture the X-ray beam passing through the object 600 for generating images of the object 600.

To acquire the foregoing images of the object 600, the irradiation source 110 and the image detector 120 are driven to be moved along a predetermined path 500. Since the irradiation source 110 is driven to be moved along the predetermined path 500, the image detector 120 can capture the X-ray beam passing through the object 600 from different angles so as to generate images of the object 600. By analyzing the images of the object 600, defects of the object 600 can be found.

Figure 2:
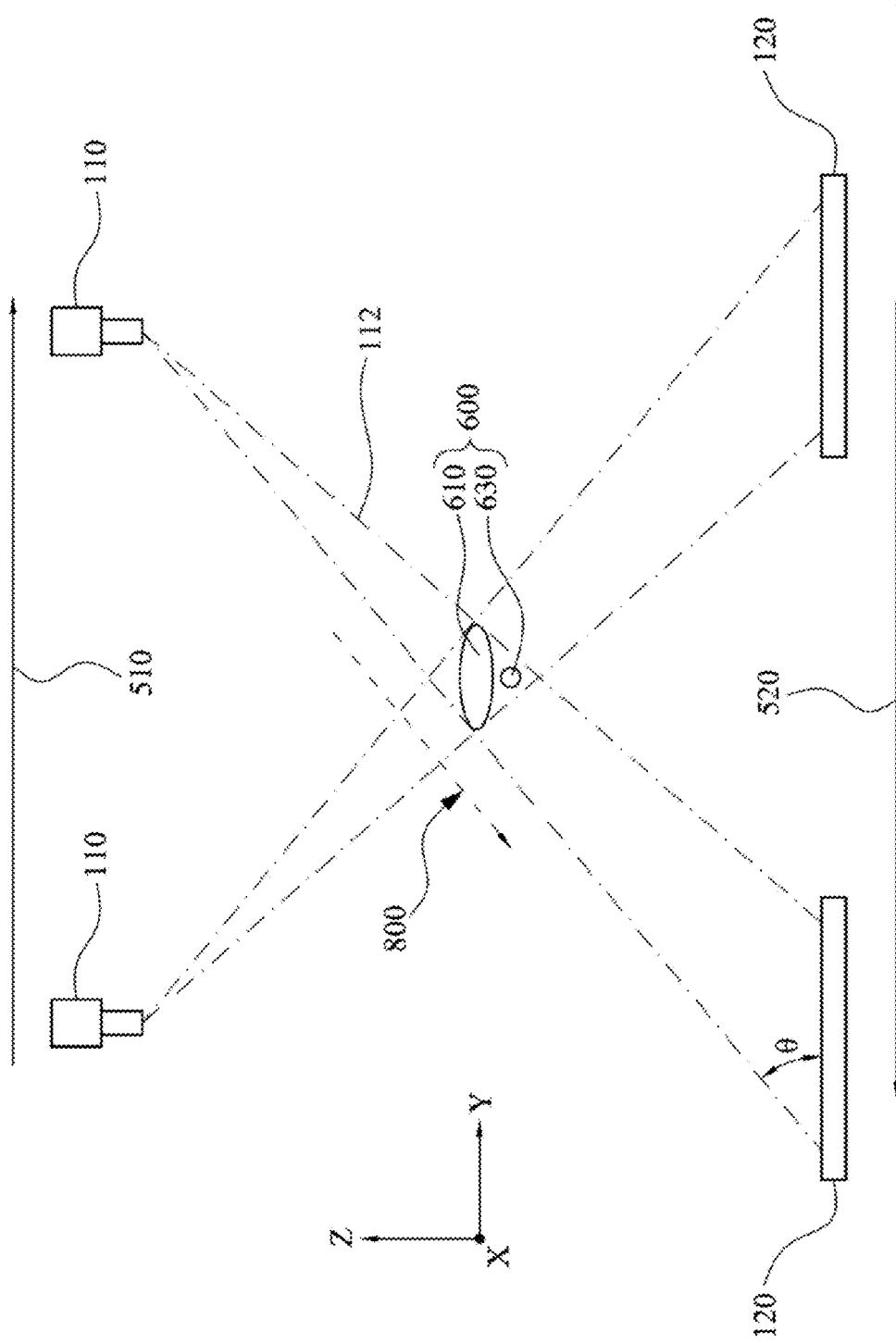
FIG. 2 is an operational diagram of an inspection system according to embodiments of the present invention.

Reference is now made to FIG. 2 which is an operational diagram of an inspection system according to embodiments of the present invention. As can be seen in FIG. 2, the irradiation source 110 and the image detector 120 are driven to be moved in different directions. For example, the irradiation source 110 is driven to be moved along a path 510, the image detector 120 is driven to be moved in a path 520, and the heading directions of the path 510 and the path 520 are opposite to each other. Compared with the irradiation source 110 and the image detector 120 being driven to be moved in the same direction, the angle θ between Y direction and the direction 800 of the irradiation from the irradiation source 110 in FIG. 2 is greater, and the image detector 120 can capture more irradiation from different angles for generating more images. Therefore, the analytic result of the object 600 is more precise.

Figure 3:
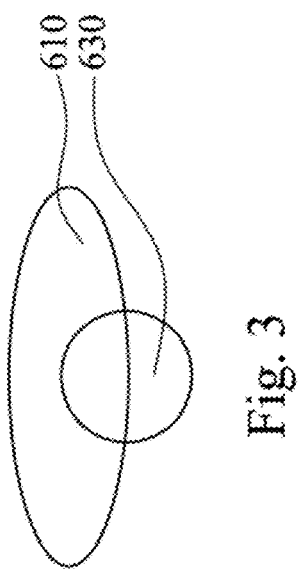
FIG. 3 is an inspection result diagram of an inspection system according to embodiments of the present invention.

Referring to FIG. 2, the object 600 includes two portions, for example, a first portion 610 and a second portion 630. However, as can be seen in FIG. 3, which is an inspection result of the object 600 generated by the inspection system, the images of the first portion 610 and the second portion 630 are overlapped with each other. According to the analytic result of the images of the object 600 in FIG. 3, the object 600 will be regarded as having only one portion.

The object 600, for example, can be a printed circuit board (PCB); if the object 600 has two portions, there may be a defect between the foregoing two portions. Hence, if the object 600 is regarded as having only one portion based on the analytic result of the images in FIG. 3, the defect between the first portion 610 and the second portion 630 of the object 600 may be ignored. That is to say, the defect exists in the PCB may be ignored.

Figure 4:
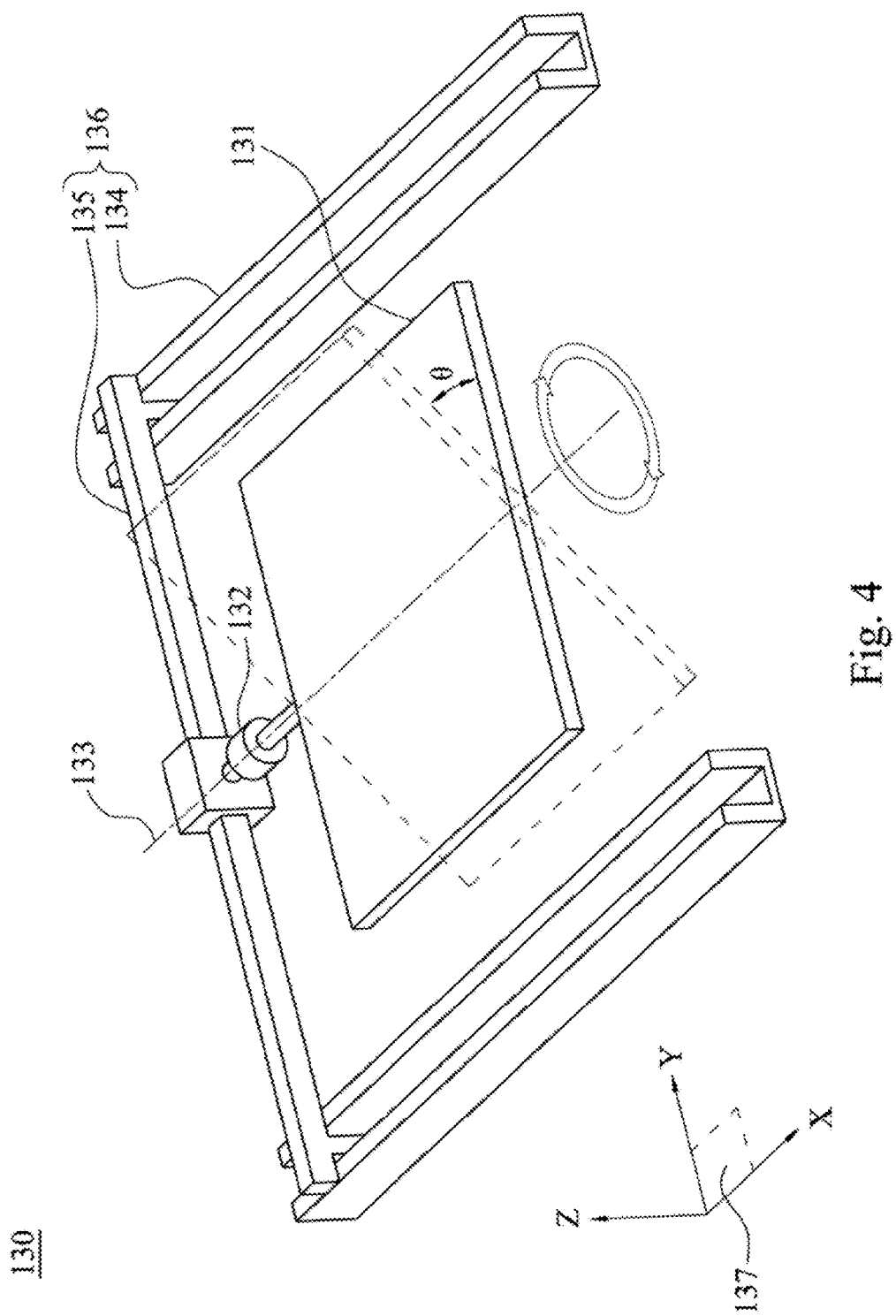
FIG. 4 is a schematic diagram of a portion of an inspection system according to embodiments of the present invention.

To prevent ignoring the above-mentioned defect, the placement device 130 of the inspection system further includes a carrier 131 and a rotation mechanism 132 as shown in FIG. 4, which is a schematic diagram of a portion of the inspection system according to embodiments of the present invention. As can be seen in FIG. 4, the rotation mechanism 132 is configured to be connected to the carrier 131. In operations, the carrier 131 is configured to carry at least one object, and the rotation mechanism 132 is configured to rotate the carrier 131. Since the object carried by the carrier 131 can be rotated by the rotation mechanism 132, the image detector 120 may capture even more irradiation from different angles for generating much more images. Hence, the analytic result of the object is much more precise, and every defect existed in the object can be found out.

Figure 5:
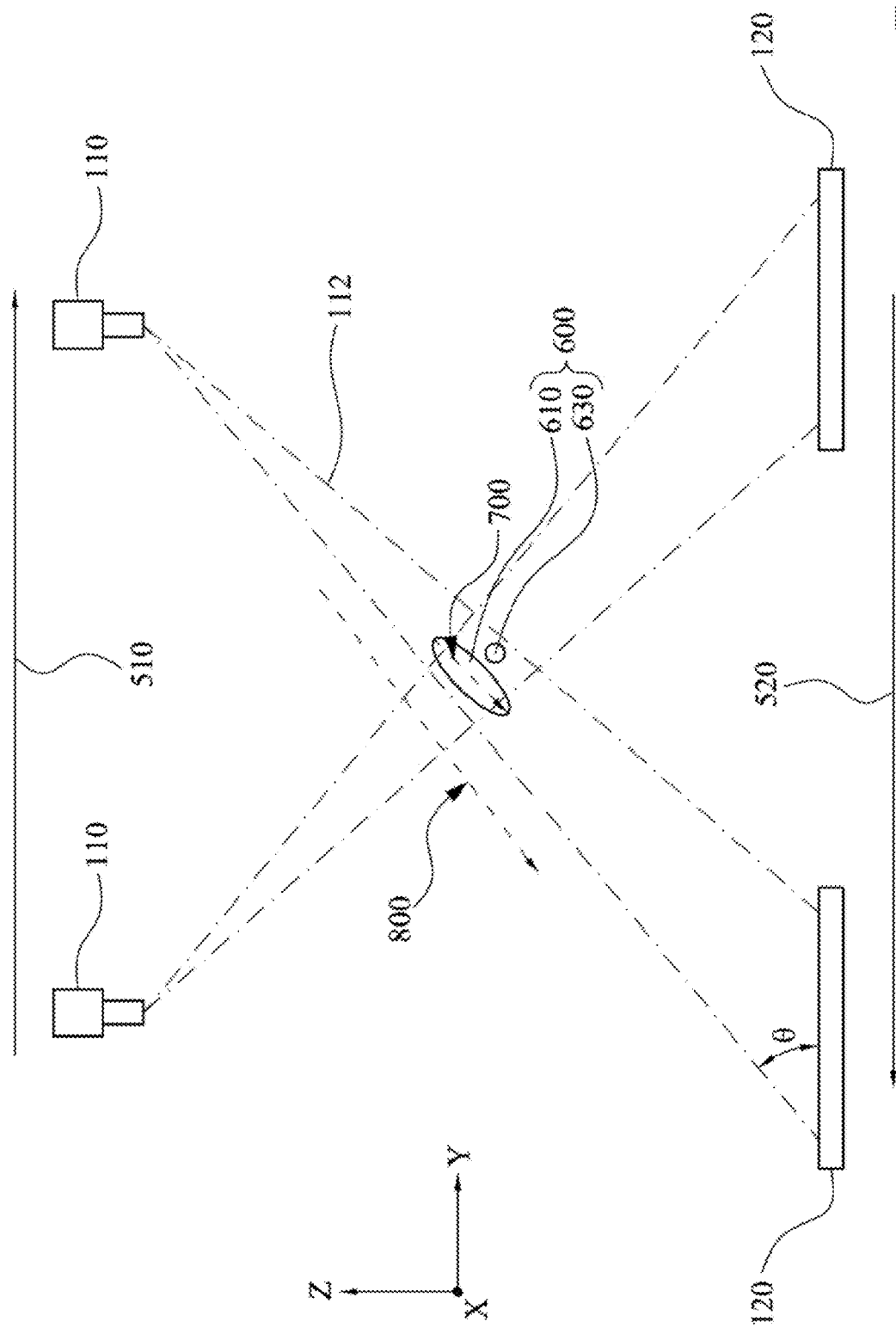
FIG. 5 is an operational diagram of an inspection system according to embodiments of the present invention.

FIG. 5 is an operational diagram of an inspection system according to embodiments of the present invention. Compared with the inspection system in FIG. 2, the inspection system in FIG. 5 further includes the rotation mechanism 132 as shown in FIG. 4 for rotating the carrier 131. Therefore, if the irradiation source 110 is configured to irradiate X-ray beam 112 in a first direction 800, the rotation mechanism 132 is configured to rotate the carrier 131 to a second direction 700 such that the first direction 800 is parallel to the second direction 700. As such, the X-ray beam 112 passes through a lateral side of the object 600, and the image detector 120 is configured to detect the X-ray beam 112 passing through the lateral side of the object 600 for obtaining a later view of the object 600.

By the inspection operation in FIG. 5, the inspection result is as shown in FIG. 6. Since the later view of the object 600 can be obtained, the images of the first portion 610 and the second portion 630 of the object 600 are not overlapped with each other. Hence, each portion of the object 600 can be clearly recognized by the inspection system, and the defect existed between the portions of the object 600 is therefore found out.

Reference is now made to FIG. 4. In another embodiment, the rotation mechanism 132 is configured to control the carrier 131 to rotate a predetermined angle θ along an axis 133. For example, if the axis 133 is X-axis and the carrier 131 is located at a plane 137 composed of X-axis and Y-axis, the rotation mechanism 132 can control the carrier 131 to rotate from the plane 137 the predetermined angle θ along X-axis. In some embodiments, the predetermined angle θ can be within thirty degrees. In still another embodiment, the predetermined angle θ can be within twenty degrees. In yet another embodiment, the predetermined angle θ can be within ten degrees.

Reference is now made to both FIG. 4 and FIG. 5. In some embodiments, the axis 133 is disposed in X direction as shown in FIG. 4. Besides, the irradiation source 110 is configured to irradiate X-ray beam 112 in a direction 800 along the YZ plane as shown in FIG. 5. Hence, the direction 800 of the X-ray beam 112 is perpendicular to the axis 133. Therefore, the object can be rotated by the rotation mechanism 132 as shown in FIG. 4 along X-axis so as to let the lateral side of the object 600 face the irradiation source 110 as shown in FIG. 5. The X-ray beam 112 therefore passes through the lateral side of the object 600. Subsequently, the X-ray beam 112 passing through the object 600 is captured by the image detector 120 for obtaining the later view of the object 600. By analyzing the later view of the object 600, each portion of the object 600 can be clearly recognized by the inspection system, and the defect existed between the portions of the object 600 is therefore found out.

Regarding FIG. 4, in some embodiments, the placement device 130 further includes a shifting mechanism 136, and the shifting mechanism 136 is configured to be connected to the rotation mechanism 132 and shift the rotation mechanism 132. In one embodiment, the shifting mechanism 136 includes a track 134 and a traverse 135. The traverse 135 can be connected to the rotation mechanism 132, and the traverse 135 can be slipped through the track 134 along X-axis. Since the traverse 135 can be slipped through the track 134 along X-axis, the rotation mechanism 132 connected with the traverse 135 can also be shifted along X-axis.

Referring to FIG. 1, in one embodiment, the irradiation source 110 and the image detector 120 are driven dependently for obtaining the images of the object 600. Reference is now made to both FIG. 4 and FIG. 5. In another embodiment, the irradiation source 110, the image detector 120, the carrier 131, and the rotation mechanism 132 are driven independently. As such, the image detector 120 may capture even more irradiation from different angles for generating much more images for enhancing the precision of the analytic result of the object 600.

In some embodiments, the rotation mechanism 110 can be at least one of a stepping motor and a servomotor. In another embodiment, the image detector 120 can be a charge couple device (CCD).

Figure 7C:
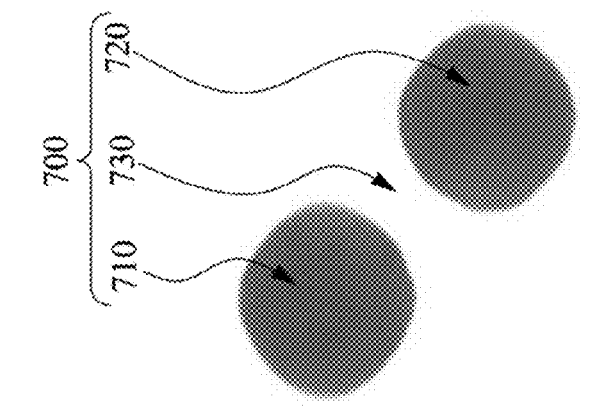
FIG. 7C is an inspection result diagram of a structure carried by an inspection system according to embodiments of the present invention.
Figure 7B:
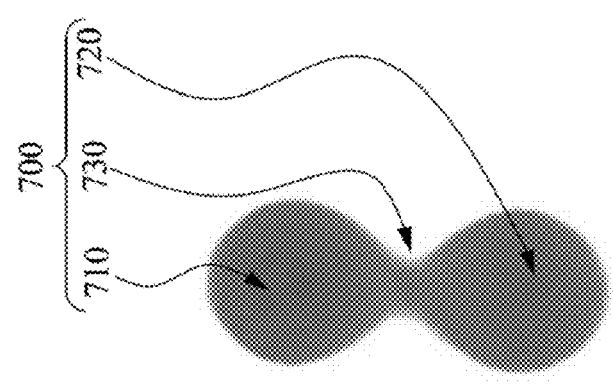
FIG. 7B is an inspection result diagram of a structure carried by an inspection system according to embodiments of the present invention.
Figure 7A:
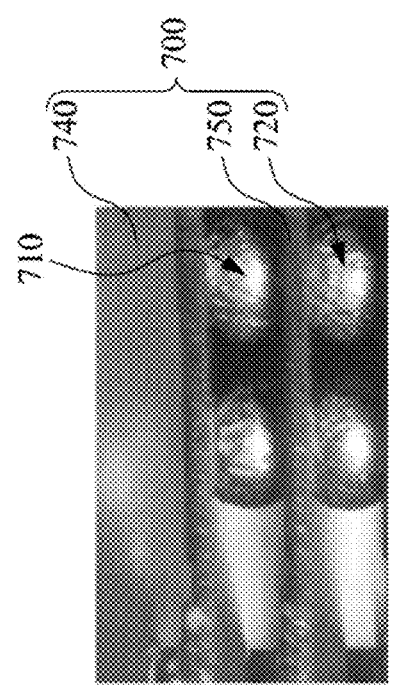
FIG. 7A is a schematic diagram of a structure carried by an inspection system according to embodiments of the present invention.

FIG. 7A is a schematic diagram of a structure 700 carried by an inspection system according to embodiments of the present invention. The structure 700 as shown in FIG. 7A is a package on package (POP) structure, and the structure 700 includes two balls 710, 720 and two layers 740, 750. By the inspection of the inspection system, the inspection result diagrams of the structure 700 are shown in FIG. 7B and FIG. 7C. Firstly, the inspection result diagram in FIG. 7B is obtained by the inspection system without the carrier 131 and the rotation mechanism 132 of the placement device 130 in FIG. 4. As can be seen in FIG. 7B, the images of the balls 710, 720 are overlapped with each other, and a false image 730 is formed. According to the analytic result of the images in FIG. 7B, the structure 700 is regarded as having only one portion.

Compared with FIG. 7B the inspection result diagram in FIG. 7C is obtained by the inspection system with the carrier 131 and the rotation mechanism 132 of the placement device 130 in FIG. 4. As can be seen in FIG. 7C, the images of the balls 710, 720 of the structure 700 are not overlapped with each other, and there is no false image 730. Hence, each balls of the structure 700 can be clearly recognized by the inspection system.

Figure 8C:
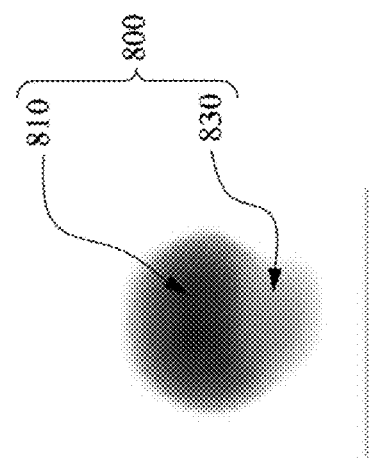
FIG. 8C is an inspection result diagram of a structure carried by an inspection system according to embodiments of the present invention.
Figure 8B:
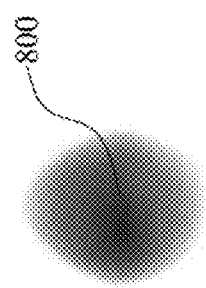
FIG. 8B is an inspection result diagram of a structure carried by an inspection system according to embodiments of the present invention.
Figure 8A:
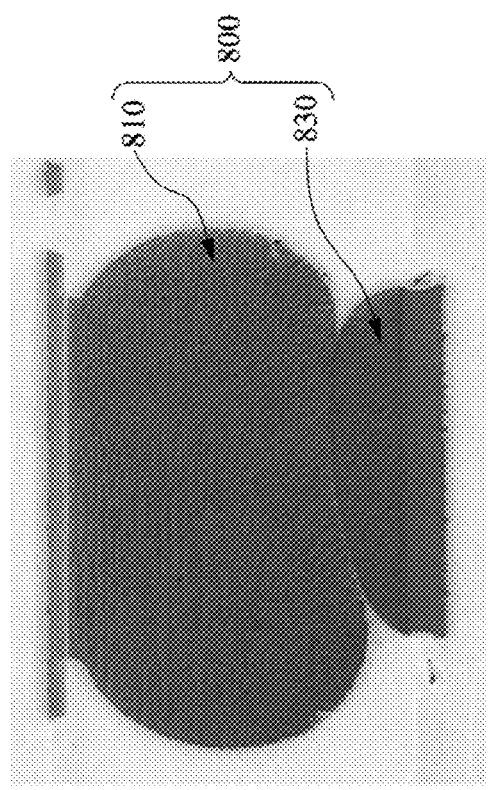
FIG. 8A is a schematic diagram of a structure carried by an inspection system according to embodiments of the present invention.

FIG. 8A is a schematic diagram of a structure 800 carried by an inspection system according to embodiments of the present invention. The structure 800 as shown in FIG. 8A is a head in pillow (HIP) formed in a ball grid array (BGA), and the structure 800 includes a tin ball 810 and a tin paste 830. By the inspection of the inspection system, the inspection result diagrams of the structure 800 are shown in FIG. 8B and FIG. 8C. Firstly, the inspection result diagram in FIG. 8B is obtained by the inspection system without the carrier 131 and the rotation mechanism 132 of the placement device 130 in FIG. 4. As can be seen in FIG. 8B, the images of the tin ball 810 and the tin paste 830 are overlapped with each other. According to the analytic result of the images in FIG. 8B the structure 800 is regarded as having only one portion. Hence, the HIP in the structure 800 may be ignored.

Compared with FIG. 8B the inspection result diagram in FIG. 8C is obtained by the inspection system with the carrier 131 and the rotation mechanism 132 of the placement device 130 in FIG. 4. As can be seen in FIG. 8C, the images of the tin ball 810 and the tin paste 830 are not overlapped with each other. Hence, the tin ball 810 and the tin paste 830 of the structure 800 can be clearly recognized by the inspection system, and the HIP existed in the structure 800 can be found out.

Figure 9:
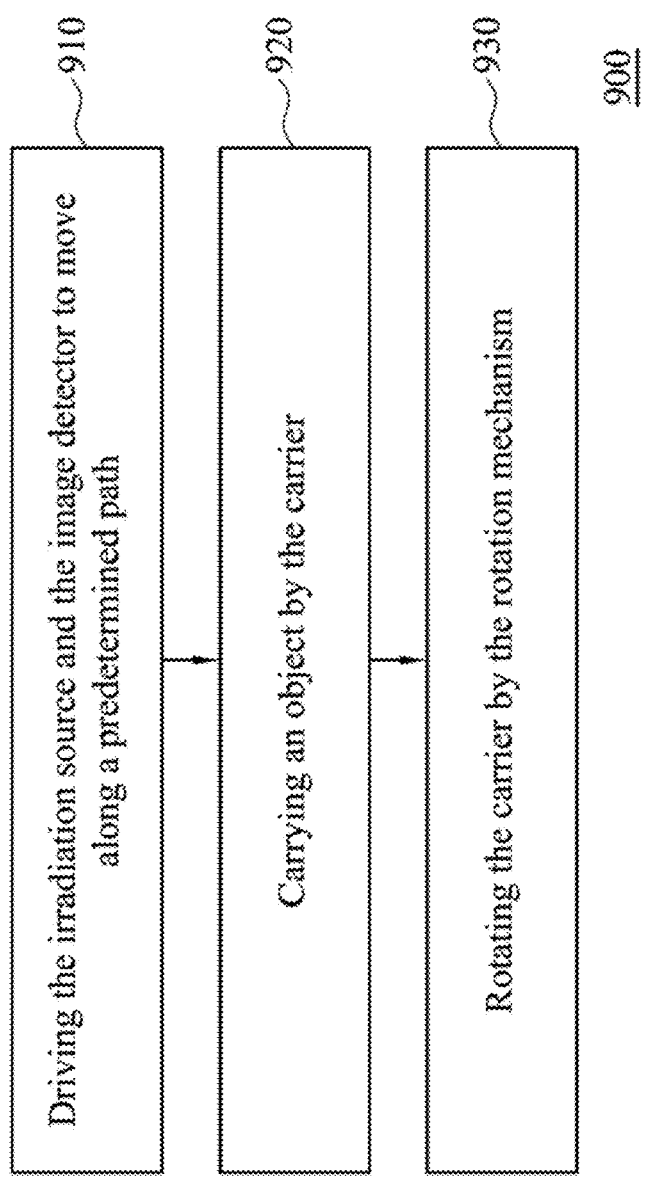
FIG. 9 is a flow diagram illustrating the process steps of a method for controlling an inspection system according to embodiments of the present disclosure.

FIG. 9 is a flow diagram illustrating process steps of a method 900 for controlling an inspection system according to embodiments of the present disclosure. The inspection system includes an irradiation source, an image detector, and a placement device. Furthermore, the placement device includes a carrier and a rotation mechanism. With respect to connections, the placement device is configured to be disposed between the irradiation source and the image detector. The method 900 for controlling the inspection system includes the steps of:

Step 910: driving the irradiation source and the image detector to move along a predetermined path;

Step 920: carrying an object by the carrier; and

Step 930: rotating the carrier by the rotation mechanism.

For facilitating the understanding of the method 900 for controlling the inspection system, reference is now made to FIG. 1, FIG. 4, and FIG. 9. The inspection system includes the irradiation source 110, the image detector 120, and the placement device 130. Furthermore, the placement device 130 includes the carrier 131 and the rotation mechanism 132. With respect to connections, the placement device 130 is configured to be disposed between the irradiation source 110 and the image detector 120. In step 910, the irradiation source 110 and the image detector 120 are driven to be moved along a predetermined path 500. Referring to step 920, the carrier 131 is configured to carry the object 600. In step 930, the rotation mechanism 132 is configured to rotate the carrier 131.

In one embodiment, the method 900 for controlling the inspection system further includes the steps of: irradiating X-ray beam in a first direction by the irradiation source; and rotating the carrier to a second direction by the rotation mechanism such that the first direction is parallel to the second direction. For facilitating the understanding of the method 900 for controlling the inspection system, reference is now made to FIG. 5. If the irradiation source 110 is configured to irradiate X-ray beam 112 in a first direction 800, the rotation mechanism 132 is configured to rotate the carrier 131 to a second direction 700 such that the first direction 800 is parallel to the second direction 700.

In another embodiment, the method 900 for controlling the inspection system further includes the step of: detecting the X-ray beam passing through the object for obtaining a later view of the object by the image detector. For facilitating the understanding of the method 900 for controlling the inspection system, reference is now made to FIG. 5. The image detector 120 is configured to detect the X-ray beam 112 passing through a lateral side of the object 600 for obtaining a later view of the object 600.

In still another embodiment, the method 900 for controlling the inspection system further includes the step of: controlling the carrier to rotate a predetermined angle along an axis by the rotation mechanism. For facilitating the understanding of the method 900 for controlling the inspection system, reference is now made to FIG. 4. The rotation mechanism 132 is configured to control the carrier 131 to rotate a predetermined angle θ along an axis 133.

In yet another embodiment, the method 900 for controlling the inspection system further includes the step of: irradiating X-ray beam in a direction by the irradiation source, wherein the direction of the X-ray beam is perpendicular to the axis. For facilitating the understanding of the method 900 for controlling the inspection system, reference is now made to both FIG. 4 and FIG. 5. The irradiation source 110 is configured to irradiate X-ray beam 112 in a direction 800, and the direction 800 of the X-ray beam 112 is perpendicular to the axis 133.

In still another embodiment, the method 900 for controlling the inspection system further includes the steps of: shifting the rotation mechanism along a shifting mechanism. For facilitating the understanding of the method 900 for controlling the inspection system, reference is now made to FIG. 4. The rotation mechanism 132 is shifted along a shifting mechanism 136.

In yet another embodiment, the method 900 for controlling the inspection system further includes the step of: driving the irradiation source and the image detector dependently. For facilitating the understanding of the method 900 for controlling the inspection system, reference is now made to FIG. 1. The irradiation source 110 and the image detector 120 are driven dependently for obtaining the images of the object 600.

In still another embodiment, the method 900 for controlling the inspection system further includes the steps of driving the irradiation source, the image detector, the carrier, and the rotation mechanism independently. For facilitating the understanding of the method 900 for controlling the inspection system, reference is now made to both FIG. 4 and FIG. 5. The irradiation source 110, the image detector 120, the carrier 131, and the rotation mechanism 132 are driven independently. As such, the image detector 120 may capture even more irradiation from different angles for generating much more images for enhancing the precision of the analytic result of the object 600.

In view of the above embodiments of the present disclosure, it is apparent that the application of the present invention has the advantages as follows. Embodiments of the present disclosure provide an inspection system and method 900 for controlling the same to improve the problem that if one object is blocked by another from X-ray beam, said object cannot be detected by the X-ray laminography system.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An inspection system, comprising:
an irradiation source;
an image detector, wherein the irradiation source is driven to be moved in a first path, and the image detector is driven to be moved in a second path, wherein the first path and the second path are opposite to each other; and
a placement device configured to be disposed between the irradiation source and the image detector, comprising:
a carrier configured to carry at least one object and disposed on a surface; and
a rotation mechanism configured to be connected to the carrier and rotate the carrier, wherein the rotation mechanism controls the carrier to rotate along an axis, and the axis is disposed on the surface, wherein if the irradiation source is configured to irradiate X-ray beam in a first direction, the rotation mechanism is configured to rotate the carrier to a second direction such that the first direction is parallel to the second direction;
wherein each of the at least one object comprises a first portion and a second portion, and the image detector is configured to detect a connection between the first portion and the second portion.

2. The inspection system of claim 1, wherein the image detector are configured to detect the X-ray beam passing through the object for obtaining a later view of the object.

3. The inspection system of claim 1, wherein the rotation mechanism is configured to control the carrier to rotate a predetermined angle along the axis.

4. The inspection system of claim 3, wherein the irradiation source is configured to irradiate X-ray beam in a direction, and the direction of the X-ray beam is perpendicular to the axis.

5. The inspection system of claim 3, wherein the predetermined angle is within thirty degrees.

6. The inspection system of claim 1, wherein the placement device further comprises:
a shifting mechanism configured to be connected to the rotation mechanism and shift the rotation mechanism.

7. The inspection system of claim 1, wherein the irradiation source, the image detector, the carrier, and the rotation mechanism are driven independently.

8. The inspection system of claim 1, wherein the irradiation source and the image detector are driven dependently.

9. The inspection system of claim 1, wherein the rotation mechanism comprises at least one of a stepping motor and a servomotor.

10. A method for controlling an inspection system, wherein the inspection system comprises an irradiation source, an image detector, and a placement device configured to be disposed between the irradiation source and the image detector, and the placement device comprises a carrier and a rotation mechanism, wherein the carrier is disposed on a surface, wherein the method comprises:
driving the irradiation source to move in a first path;
driving the image detector to move in a second path, wherein the first path and the second path are opposite to each other;
carrying an object by the carrier, wherein the object comprises a first portion and a second portion;
rotating the carrier by the rotation mechanism, and controlling the carrier to rotate along an axis by the rotation mechanism, wherein the axis is disposed on the surface;
irradiating X-ray beam in a first direction by the irradiation source;
rotating the carrier to a second direction by the rotation mechanism such that the first direction is parallel to the second direction; and
detecting a connection between the first portion and the second portion.

11. The method of claim 10, further comprising:
detecting the X-ray beam passing through the object for obtaining a later view of the object by the image detector.

12. The method of claim 10, further comprising:
controlling the carrier to rotate a predetermined angle along the axis by the rotation mechanism.

13. The method of claim 12, further comprising:
irradiating X-ray beam in a direction by the irradiation source, wherein the direction of the X-ray beam is perpendicular to the axis.

14. The method of claim 12, wherein the predetermined angle is within thirty degrees.

15. The method of claim 10, further comprising:
shifting the rotation mechanism along a shifting mechanism.

16. The method of claim 10, further comprising:
driving the irradiation source, the image detector, the carrier, and the rotation mechanism independently.

17. The method of claim 10, further comprising:
driving the irradiation source and the image detector dependently.

18. The method of claim 10, wherein the rotation mechanism comprises at least one of a stepping motor and a servomotor.

\* \* \* \* \*